United States Patent
Kotar-Jordan et al.

(10) Patent No.: US 7,906,642 B2
(45) Date of Patent: Mar. 15, 2011

(54) ISOPROPANOL WATER SOLVATE OF OLANZAPINE

(75) Inventors: Berta Kotar-Jordan, Kostanjevica na Krki (SI); Roman Lenarsic, Ljubljana (SI); Marija Grcman, Velika Loka (SI); Matej Smrkolj, Izlake (SI); Anton Meden, Lukovica (SI); Igor Simonic, Straza (SI); Rok Zupet, Ljubljana (SI); Joze Gnidovec, Otocec (SI); Primoz Benkic, Trzin (SI)

(73) Assignee: KRKA, Tovarna Zdravil, D.D., Novo mesto (SI)

( * ) Notice: Subject to any disclaimer, the term of this patent is extended or adjusted under 35 U.S.C. 154(b) by 1114 days.

(21) Appl. No.: 10/591,831

(22) PCT Filed: Mar. 7, 2005

(86) PCT No.: PCT/EP2005/002389
§ 371 (c)(1),
(2), (4) Date: Oct. 23, 2006

(87) PCT Pub. No.: WO2005/085256
PCT Pub. Date: Sep. 15, 2005

(65) Prior Publication Data
US 2007/0191348 A1    Aug. 16, 2007

(30) Foreign Application Priority Data

Mar. 8, 2004 (SI) .................................. 200400073
Dec. 14, 2004 (DE) ......................... 10 2004 060 412

(51) Int. Cl.
*C07D 495/04* (2006.01)
(52) U.S. Cl. ...................................................... 540/557
(58) Field of Classification Search ................... 540/557
See application file for complete search history.

(56) References Cited

U.S. PATENT DOCUMENTS

2006/0040920 A1* 2/2006 Kotar Jordan et al. ........ 514/220
* cited by examiner

*Primary Examiner* — Brenda L Coleman
(74) *Attorney, Agent, or Firm* — Cohen Pontani Lieberman & Pavane LLP

(57) ABSTRACT

The invention relates to a novel and well defined Oolvate form of olanzapine which contains 2 molecules of water and 1 molecule of isopropanol per 2 molecules of olanzapine, and which can be converted into other, forms of olanzapine, in particular form (I) of olanzapine, as well as processes for preparing form (I) olanzapine.

30 Claims, 2 Drawing Sheets

ISOPROPANOL WATER SOLVATE OF OLANZAPINE

PRIORITY CLAIM

This is a U.S. national stage of application No. PCT/EP2005/002389, filed on Mar. 7, 2005. Priority is claimed on the following application(s): Country: Slovenia, Application No.: P-200400073, Filed: Mar. 8, 2004; Country: Germany, Application No.: 10 2004 060 412.6, Filed: Dec. 14, 2004; the content of which is incorporated here by reference.

FIELD OF THE INVENTION

The present invention belongs to the field of organic chemistry and relates to a new mixed solvate form of 2-methyl-4-(4-methyl-1-piperazinyl)-10H-thieno [2,3-b] [1,5]benzodiazepine (hereinafter referred to by its generic name "olanzapine"), a process for its preparation and processes for the preparation of polymorphic form I of olanzapine.

BACKGROUND OF THE INVENTION

Olanzapine has shown to have high activity with regard to the central nervous system and is also useful for the treatment of schizophrenia, schizophreniform disorders, acute mania, mild anxiety states and psychosis.

Various polymorphic and pseudopolymorphic forms, such as solvates, of olanzapine have become known. Some of them are useful for conversion to other desirable forms.

The British patent GB 1 533 235 discloses antipsychotically effective thienobenzodiazepines by a generic formula which also covers olanzapine.

U.S. Pat. No. 5,229,382 discloses olanzapine explicitly. The described process for its synthesis involves a crystallization from acetonitrile.

EP-B-733 635 claims crystalline form II olanzapine, and this polymorphic form is said to be more stable than the material obtained according to U.S. Pat. No. 5,229,382 which is designated "form I olanzapine". Both the form I and the form II of olanzapine are characterized by e. g. X-ray data. The preparation of the more stable form II of olanzapine is effected by dissolving technical grade olanzapine in ethyl acetate and crystallization from the resulting solution by any conventional process such as seeding, cooling, scratching the glass of the reaction vessel or other common techniques.

WO 02/18390 discloses the monohydrate form I and the dihydrate form I of olanzapine, a process for production thereof and a process for production of form I of olanzapine which comprises the steps of stirring olanzapine monohydrate form I or crude olanzapine or form II of olanzapine in methylene chloride at reflux, cooling, filtering and drying. It is also described that a repeating of the process described in U.S. Pat. No. 5,229,382 Example 1, subexample 4 did not lead to formation of form I of olanzapine.

WO 03/101997 relates to processes for preparation of form I of olanzapine by regulation of the pH-value of the solution.

WO 03/055438 discloses the preparation of form I olanzapine by crystallization from ethanol and subsequent conversion of the obtained ethanol solvate.

U.S. Pat. No. 5,637,584 discloses the (mono)methylene chloride solvate form of olanzapine and a method for its conversion to the polymorphic form I of olanzapine.

EP-B-733 634 discloses three specific solvates of olanzapine, namely the methanol, ethanol and 1-propanol solvates and a process for production of form II olanzapine by drying such a solvate.

WO 03/097650 describes two new mixed solvate forms, the water/methylene chloride solvate and the water/DMSO solvate, methods for preparing them, and their transformation to polymorphic form I.

WO 2004/006933 discloses a process for the preparation of form I olanzapine, as well as various pseudopolymorphic forms, namely the isopropanol solvate, and the acetonitrile/methylene chloride/water and acetonitrile/water mixed solvates of olanzapine, and the polymorphic form A.

However, the prior art processes for preparation of form I olanzapine often do not lead to a satisfactory yield. Moreover, they result in olanzapine having a purity which is not satisfactory for the preparation of pharmaceutical formulations as impurities are present which are difficult to be removed. This is often caused by undesired impurities which are formed upon preparation of precursors and are therefore, upon conversion of the precursors to form I olanzapine, introduced in the final product.

Further, prior art processes often do not allow use of higher temperatures without impairing yield or purity of the form I olanzapine.

Consequently, there is still a need for improved processes to prepare purified olanzapine form I in a satisfactory yield.

Further, there is a need for precursors which allow the easy preparation of polymorphic forms of olanzapine or the conversion to other forms of olanzapine in a high purity.

These problems are solved by the present invention.

DETAILED DESCRIPTION OF THE INVENTION

The invention relates to a water/isopropanol mixed solvate which contains 2 molecules of water and 1 molecule of isopropanol per 2 molecules of olanzapine.

The solvate according to the invention was subjected to an x-ray structure analysis. Single crystal x-ray diffraction data were collected at room temperature on a Nonius Kappa CCD diffractometer by means of the Nonius Collect Software. The structure was solved by using SIR97 (direct methods) and the refinement was performed with X'tal software. The crystallographic data for the olanzapine isopropanol/water mixed solvate, particularly the interplanar distances (a, b, c) and angles ($\alpha$, $\beta$, $\gamma$), are indicated in Table 1.

TABLE 1

| Space group | C2/c (No. 15) |
|---|---|
| a | 24.55 Å |
| b | 12.51 Å |
| c | 15.31 Å |
| $\alpha$ | 90° |
| $\beta$ | 125.3° |
| $\gamma$ | 90° |
| R | 0.059 |

Figure 1:
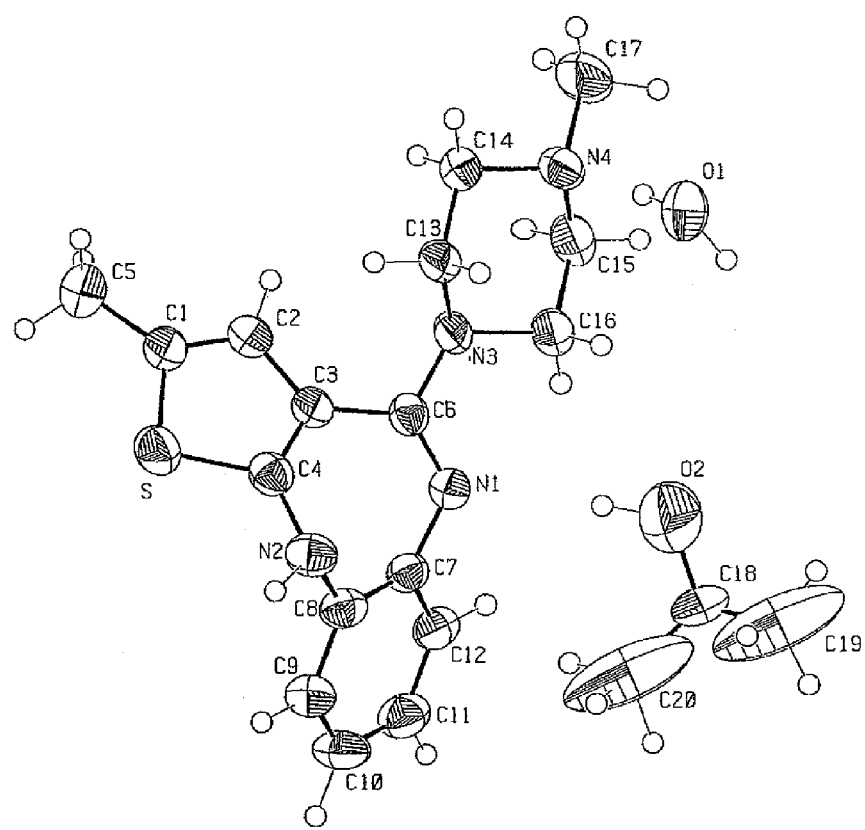
FIG. 1 The x-ray structure of the isopropanol/water mixed solvate of olanzapine.

Thus, the invention also relates to the isopropanol/water mixed solvate of olanzapine characterized by the x-ray structure shown in FIG. 1. FIG. 1 shows the ORTEP view of the asymmetric unit of the solvate according to the invention which corresponds to the formula $C_{17}H_{20}N_4S \cdot H_2O \cdot \frac{1}{2}(C_3H_7OH)$. It is to be noted the population of the disordered isopropanole molecule in FIG. 1 is 0.50. Thus, an isopropanol molecule occurs only with every second molecule of olanzapine.

Further, the solvate according to the invention is characterized by a NMR spectrum in $CDCl_3$ showing peaks at approximately 1.20 ppm, 2.20-2.40 ppm and 4.03 ppm. Preferably, the solvate is characterized by the NMR spectrum shown in FIG. 2.

The NMR spectra were obtained using a Varian UNITY+ 300 (300 MHz) spectrometer and $CDCl_3$ as solvent with tetramethylsilane as internal standard.

Figure 2:
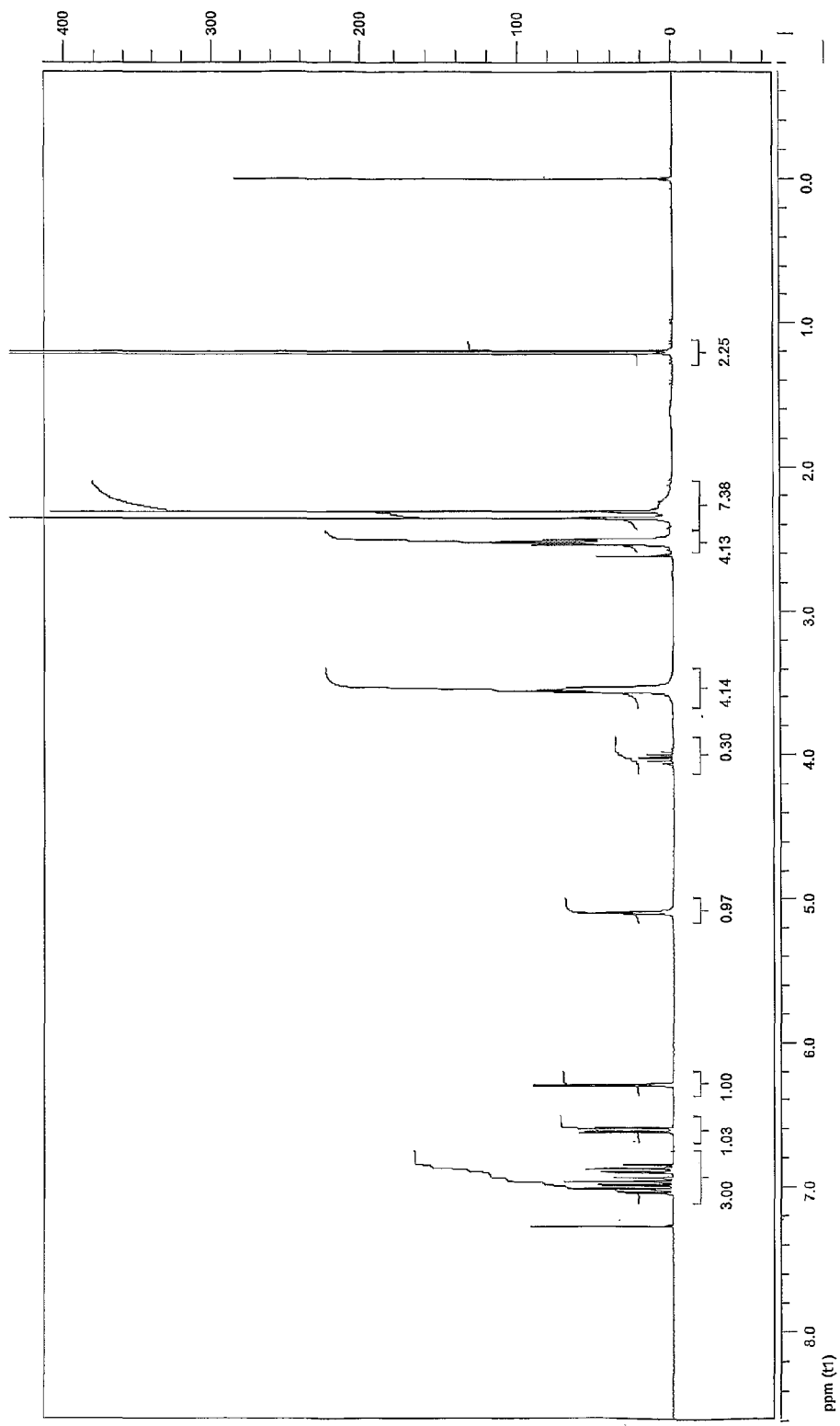
FIG. 2 The NMR spectrum of the isopropanol/water mixed solvate of olanzapine.

FIG. 2 shows the NMR spectrum of the solvate according to the invention. The peaks were assigned as follows ($^1$H NMR; $CDCl_3$, 300 MHz):

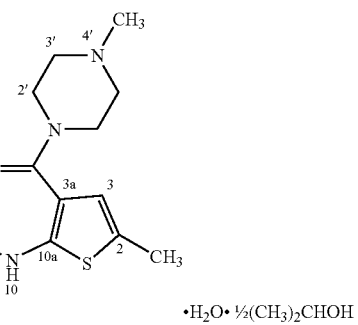

·$H_2O$· ½$(CH_3)_2CHOH$

| Chemical shift δ | Assignement |
|---|---|
| 1.20(3H, d) | $CH_3$-isopropanol |
| 2.30(3H, s) | 4'-$CH_3$ |
| 2.34(3H, s) | 2-$CH_3$ |
| 2.20-2.40(2H, br s) | H-water |
| 2.49(4H, m) | 3'-$CH_2$ |
| 3.52(4H, m) | 2'-$CH_2$ |
| 4.03(0.5H, dq) | CH-isopropanol |
| 5.02(H, broad s) | 10-NH |
| 6.29(H, broad s) | 3-CH |
| 6.29-7.05(4H, m) | 6,7,8,9-H |

The solvate according to the invention is prepared by a process which comprises crystallizing it from a solvent mixture comprising isopropanol and water in a ratio of at least 9 to 1, preferably at least 20 to 1 and most preferred at least 35 to 1 parts by volume.

It has been shown particularly advantageous if the crystallization is effected by adding the water to a solution comprising olanzapine and the isopropanol.

It has unexpectedly been found that the preparation of the olanzapine water-isopropanol mixed solvate can easily be accomplished if olanzapine is crystallized by using a solvent mixture which comprises isopropanol and water. In this way persistent impurities are removed from the active compound and the dissolved olanzapine can also be recovered from filtrates in an easy manner.

The olanzapine used as a starting material for the preparation of the water/isopropanol mixed solvate according to the invention can be in any form, e.g. it can be used when it is contained in a reaction solution or in a filtrate in combination with other solvents, or it can be in crude, anhydrous or any solvated or hydrated form or a mixture thereof.

In a preferred embodiment, the water/isopropanol mixed solvate according to the invention is prepared from a reaction mixture. An example is given in the following.

For this purpose, a mixture of 4-amino-2-methyl-10H-thieno [2,3-b] [1,5]benzodiazepine hydrochloride and 1-methylpiperazine is heated in high boiling solvents, e.g. dimethylsulfoxide or toluene, or mixtures thereof, preferably under reflux, until the reaction is completed, preferably 3 to 12 hours. The solution is then cooled, preferably to temperatures ranging from 90° C. to room temperature, and optionally a part of the reaction mixture is distilled off, preferably under vacuum, at temperatures ranging from room temperature to 90° C., preferably at 50° C. to 90° C. To the obtained solution isopropanol and water are separately added in any order or a mixture thereof is added. Preferably, isopropanol is added first, followed by the addition of water to initiate crystallization. Preferably, the clear solution is cooled to temperatures from boiling temperature to 10° C., and water is added to start crystallization. The product is then filtered off, washed with isopropanol, dried at room temperature under vacuum to a constant weight, and the water/isopropanol mixed solvate according to the invention is obtained.

In a further preferred embodiment, the water/isopropanol mixed solvate of olanzapine is prepared from mother liquors containing olanzapine and for example methylene chloride, or from a methylene chloride solvate. form. An example is given in the following.

In such a case, the solvent is optionally distilled off, preferably under vacuum, and subsequently isopropanol and water are separately added in any order or a mixture thereof is added. Preferably, isopropanol is added first, followed by the addition of water to initiate crystallization. After the crystallization has been completed, the precipitate is filtered off and dried.

In a further preferred embodiment, the water/isopropanol mixed solvate is prepared from crude olanzapine, or from olanzapine in anhydrous or any solvated or hydrated form, or mixtures thereof. An example is given in the following.

In such a case, the olanzapine is dissolved by heating in a mixture of isopropanol and water, or in either isopropanol or water with the other solvent being subsequently added. The obtained clear solution is cooled to temperatures from boiling temperature to 10° C., and water is added to start crystallization. The product is then filtered off, washed with isopropanol, dried at room temperature under vacuum to a constant weight, and the water-isopropanol mixed solvate according to the invention is obtained.

The water-isopropanol mixed solvate obtained by any one of the above processes can optionally be recrystallized. During the crystallization or precipitation procedure of any process, ethylenediaminotetraacetic acid disodium salt can be added and, after stirring, undissolved material be hot filtered.

The water-isopropanol mixed solvate according to the invention prepared by any of the above processes is of high quality and substantially free of impurities and is therefore ideally suited for the preparation of various other highly pure solvates, hydrates or anhydrous forms or mixtures thereof.

The water-isopropanol mixed solvate according to the invention is particularly useful for the preparation of olanzapine form I in a high purity.

Thus, the invention also relates to a process for the preparation of form I olanzapine, wherein the isopropanol/water mixed solvate of olanzapine according to the invention is used.

Form I of olanzapine is rather difficult to be prepared in substantially pure form, because formation of the thermodynamically more stable form II is favoured. According to the process of the present invention pure form I could be obtained which is in particular substantially free from form II and solvates.

In a preferred embodiment of the process, in a step (a) the isopropanol/water mixed solvate is converted to a methylene chloride solvate of olanzapine, and in a step (b) the methylene chloride solvate is converted to form I olanzapine.

It is advantageous if in step (a) a solution of the isopropanol/water mixed solvate in methylene chloride is prepared, the solvent is partly evaporated and the remaining solution is cooled.

It is also preferred if in step (a) a solution of the isopropanol/water mixed solvate in methylene chloride is prepared, a drying agent is added to the solution, the drying agent is removed from the mixture and the methylene chloride solvate of olanzapine is recovered. Preferably, the mixture is stirred for some time and filtered, and finally, the product is recovered, e. g. by crystallization after cooling. A particularly useful drying agent is anhydrous $CaSO_4$.

In a further process for effecting step (a), the water-isopropanol mixed solvate according to the invention is suspended in methylene chloride and the suspension is heated until a clear solution is obtained. Then a part of the solvent is evaporated under vacuum or optionally at atmospheric pressure or a combination thereof at temperatures ranging from the boiling point of the solution to −30° C. to precipitate olanzapine methylene chloride solvate, which can be isolated by filtration. Alternatively, the heated solution can be cooled to temperatures from room temperature to −30° C. to precipitate the olanzapine methylene chloride solvate.

In another typical process for effecting step (a), the water-isopropanol mixed solvate is suspended in methylene chloride and the suspension is heated to 35° C. to obtain a clear solution. Subsequently, a drying agent, preferably Drierite ($CaSO_4$ anhydrous), is added, and the desired product is recovered in conventional manner.

Optionally, a seeding with higher amounts of crystalline methylene chloride solvate is effected. Also olanzapine form I is a suitable seeding material.

It is preferred to use as methylene chloride solvate in step (b) the methylene chloride hemisolvate. For its preparation it is usually necessary to dry the product in a vacuum at room temperature for 2 to 12 hours.

In a typical and preferred process for effecting step (b), isopropanol is added to the prepared olanzapine methylene chloride solvate in a volume (l) by weight (kg) ratio of 5:1 to 2:1, preferably 3:1 to 2:1, and the obtained suspension is stirred at a temperature of 15° C. to 35° C., in particular at room temperature, for 15 to 90 min, preferably from 30 to 60 min. Preferably, seeding with form I olanzapine can be used. The filtered product is dried under vacuum at a temperature from room temperature to 50° C. until a constant weight is achieved.

In another typical and preferred process for effecting step (b), methylene chloride solvate is suspended in isopropanol at a weight (kg) by volume (l) ratio of 1:30 to 1:2, preferably 1:15 to 1:3, which has been presaturated with olanzapine. The obtained suspension is stirred at a temperature of 5° C. to 50° C., in particular at room temperature, for 15 to 90 min, preferably from 30 to 60 min. The product is filtered off and dried under vacuum at room temperature to a constant weight, and then at 50° C. to a constant weight. Form I olanzapine is isolated.

In another typical and preferred process for effecting step (b), methylene chloride solvate is first dried under vacuum at a temperature of 30 to 55° C. for 6 to 36 hours. The obtained product is suspended in isopropanol at a weight (kg) by volume (l) ratio of 1:5 to 1:2, preferably 1:3 to 1:2. The obtained suspension is stirred at a temperature of 15° C. to 35° C., in particular at room temperature, for 15 to 60 min, preferably from 15 to 30 min. The product is filtered off and dried under vacuum at room temperature to a constant weight, and then at 50° C. to a constant weight. This process offers the advantage that it very much diminishes the possibility of formation of the undesired form II of olanzapine.

In another preferred embodiment of the process for the preparation of form I olanzapine, solid isopropanol/water mixed solvate of olanzapine according to the invention is mixed with solid olanzapine of form I and the particle size of the mixture is reduced.

Preferably the mixing and the size-reduction take place in a single step by for example grinding or milling the mixture. Grinding can take place in a mortar and for milling usual milling machines can be used.

The mixture preferably comprises up to 10% and in particular up to 5% by weight of form I olanzapine.

The obtained material is usually dried to give the desired form I olanzapine. The drying is preferably conducted in a vacuum drier at temperatures ranging from room temperature to 80° C., preferably from room temperature to 60° C. and most preferred from 40 to 50° C.

It is also preferred to process the dried material further by suspending it in isopropanol, separating the solid by filtration and drying of the solid. The dried material is preferably suspended in isopropanol in a weight (kg) to volume (l) ratio of 1:5 to 1:2, in particular 1:3 to 1:2. The suspension is preferably stirred at a temperature of 15 to 35° C., in particular at room temperature, for 15 to 60 min, in particular 15 to 30 min.

The drying is preferably conducted under vacuum at room temperature to a constant weight and then at 50° C. to a constant weight.

This simple process unexpectedly results in very high yields of form I olanzapine having a high polymorphic purity.

Further, the invention also relates to a process for the preparation of any other solvate or hydrate forms of olanzapine, or mixtures thereof, wherein the isopropanol/water mixed solvate of olanzapine according to the invention is used.

Moreover, the invention also relates to a process for the preparation of anhydrous forms of olanzapine, wherein the isopropanol/water mixed solvate of olanzapine according to the invention is used.

It has also surprisingly been found out that in the process of preparing form I olanzapine the purity of the final product can be influenced by the type of the materials which come into contact with the liquid media from which precursors or the final product is crystallized or precipitated. This has in particular been observed when using elevated temperatures in the process.

The invention therefore also relates to a process for preparing form I olanzapine wherein at least one of (a) precursors for olanzapine form I and (b) olanzapine form I. is crystallized or precipitated from a liquid medium which medium is present in a container wherein the surfaces of the container contacting the medium are comprising at least one polymer, preferably are consisting of at least one polymer.

It was unexpectedly found out that such polymer surfaces in particular diminish the likelihood of formation of the undesired form II of olanzapine, especially when using elevated temperatures. This is very beneficial since the form II is an impurity which is very difficult to be removed, if possible at all, and even small amounts thereof may function as seeding crystals which lead to formation of further amounts of the undesired form II olanzapine.

It is preferred that the precursors and/or the olanzapine form I are prepared using the isopropanol/water mixed solvate according to the invention. This leads to highly pure olanzapine form I.

The liquid medium can be a solution or dispersion which upon crystallization or precipitation leads to form I olanzapine or a precursor of form I olanzapine.

Preferably, at least one crystallization or precipitation step of a precursor is carried out such that the liquid medium is contacting the mentioned polymer surface. It is particularly preferred that such a precursor is the methylene chloride hemisolvate of olanzapine. It was found out that in particular in the crystallization or precipitation of the methylene chloride hemisolvate the likelihood of formation of the undesired form II olanzapine is diminished if carried in contact with the polymer surfaces.

In an even further preferred embodiment, the methylene chloride hemisolvate has been prepared by using the very pure isopropanol/water mixed solvate according to the invention. This accomplishes the preparation of very pure olanzapine of form I.

The container can be any equipment, like a vessel or reactor, wherein a crystallization or precipitation occurs.

It has been proven particularly useful if the polymer contains fluorine. Preferred examples are selected from polytetrafluoroethylene, e.g available under the brand Teflon, fluorinated ethylene propylene copolymer, perfluoro alkoxy polymer, or ethylene terafluoroethylene copolymer.

It is possible that only the surfaces contacting the liquid medium are comprising polymer or are consisting of polymer, but typically the whole container is made of polymer, preferably made of polytetrafluoroethylene.

The invention is in the following illustrated by means of examples.

EXAMPLES

Reparation of the Water-Isopropanol Mixed Solvate of Olanzapine

Example 1

A mixture of 4-amino-2-methyl-10H-thieno[2,3-b] [1,5] benzodiazepine hydrochloride (26.6 g), 1-methylpiperazine (92 ml), dimethylsulfoxide (120 ml) and toluene (120 ml) was refluxed for 4 hours. The solution was cooled to 95° C. and 200 ml were distilled off under vacuum. The residue was cooled to room temperature, isopropanol (180 ml) was added, and the solution was further cooled to 0° C. and water (36 ml) was added to initialize crystallization. After the crystallization was completed, the precipitate was filtered off and washed with isopropanol (20 ml). The wet product was suspended in isopropanol (200 ml) and heated to reflux to obtain a clear solution. Ethylenediaminotetraacetic acid disodium salt (3 g) was added and the suspension was stirred for one hour. Undissolved material was removed by hot filtration. The clear solution was cooled to 25° C. and water (6 ml) was added to start crystallization. The suspension was cooled to 0C and after completion of the crystallization the product was filtered off and washed with isopropanol (10 ml). The product was dried at room temperature under vacuum to a constant weight. Yield: 22.84 g. Loss on drying (140° C.): 13.6%. Water content (Karl Fischer): 5.12%.

Example 2

A mixture of 4-amino-2-methyl-10H-thieno[2,3-b] [1,5] benzodiazepine hydrochloride (26.6 g), 1-methylpiperazine (92 ml), dimethylsulfoxide (36 ml) and toluene (120 ml) was refluxed for 4 hours. The solution was cooled to 95° C. and 80 ml were distilled off under vacuum. The residue was cooled to room temperature, and isopropanol (180 ml) was added. The solution was further cooled to 0° C. and water (36 ml) was added to initialize crystallization. After the crystallization was completed, the precipitate was filtered off and washed with isopropanol (20 ml). The wet product was suspended in isopropanol (200 ml) and heated to reflux to obtain a clear solution. Ethylenediaminotetraacetic acid disodium salt (3 g) was added and the suspension was stirred for one hour. Undissolved material was removed by hot filtration. The clear solution was cooled to 35° C. and water (6 ml) was added to start crystallization. The suspension was cooled to 0° C., upon finalization of the crystallization, the product was filtered off and washed with isopropanol (10 ml) The product was dried at room temperature under vacuum to a constant weight. Yield: 21.98 g. Loss on drying (140° C.): 13.2%. Water content (Karl Fischer): 5.09%. Assay of isopropanol (GC): 8.55%.

Example 3

A mixture of 4-amino-2-methyl-10H-thieno[2,3-b][1,5] benzodiazepine hydrochloride (26.6 g), 1-methylpiperazine (92 ml), dimethylsulfoxide (36 ml) and toluene (120 ml) was refluxed for 4 hours. The solution was cooled to 95° C. and 120 ml were distilled off under vacuum. The residue was cooled to room temperature, and isopropanol (180 ml) was added. The solution was further cooled to 0° C. and water (36 ml) was added to initialize crystallization. After completion of the crystallization, the precipitate.was filtered off and washed with isopropanol (20 ml). The wet product was suspended in isopropanol (200 ml) and heated to reflux to obtain a clear solution. Ethylenediaminotetraacetic acid disodium salt (3 g) was added and the suspension was stirred for one hour. Undissolved material was removed by hot filtration. The clear solution was cooled to 35° C. and water (6 ml) was added to start crystallization. The suspension was cooled to 0° C., upon completion of the crystallization, the product was filtered off and washed with isopropanol (10 ml). The product was dried at room temperature under vacuum to a constant weight. Yield: 24.35 g. Loss on drying (140° C.): 13.5%. Water content (Karl Fischer): 5.05%.

Example 4

Anhydrous olanzapine (10 g) was suspended in isopropanol (108 ml) and heated to reflux to obtain a clear solution. The solution was slowly cooled. Water (6 ml) was added at 57° C. to start crystallization. The suspension was cooled to 0° C., upon finalization of the crystallization, the product was filtered off and washed with isopropanol (5 ml). The product was dried at room temperature under vacuum to a constant weight. Yield:

10.97 g. Loss on drying (140° C.): 13.3%. Water content (Karl Fischer): 5.13%.

Example 5

60 g of olanzapine obtained from mother liquors was suspended in isopropanol (650 ml) and heated to reflux to obtain a clear solution. Ethylenediaminotetraacetic acid disodium salt (7.9 g) was added and the suspension was stirred for one hour. Undissolved material was removed by hot filtration. The clear solution was cooled to 25° C. and water (16 ml) was added to start crystallization. The suspension was cooled to 0° C. and, upon completion of the crystallization, the product was filtered off and washed with isopropanol (50 ml). The product was dried at room temperature under vacuum to a constant weight. Yield: 57.64 g. Loss on drying (140° C.): 13.5%. Water content (Karl Fischer): 5.26%.

Example 6

The solution of 2,4-bis(4-methyl-1-piperazinyl)-3-propylidene-3H-[1,5]benzodiazepine (41.86 g, 0.11 mmol) (prepared according to WO 2004/065390), pyridinium p-toluenesulfonate (55.29 g, 0.22 .mmol) and sulfur (11.99 g, 0.374 mmol) in benzonitrile (1100 mL) was stirred at 140° C. for 11 h, cooled to 90° C. and concentrated to an oily residue. The residue was diluted with dichloromethane and isopropanol (250 mL, 1:1). The precipitate was filtered off and washed with dichloromethane and isopropanol (20 ml, 1:1). The filtrate was extracted with HCl (250 ml, 2 M). The organic phase was further extracted with HCl (2×100 ml, I M). The combined aqueous phases were cooled in an ice bath and made alkaline by using 5 M NaOH. The obtained turbid solution was left in a refrigerator over night resulting in a suspension. This was separated by filtration and washed with isopropanol (2×25 ml). The wet material was suspended in isopropanol (215 ml) and heated to reflux to obtain a clear solution. The solution was hot filtered. Water (6.5 ml) was added to induce crystallization. The obtained suspension was cooled to 0° C., and upon completion of crystallisation, the product was filtered off and washed with isopropanol (10 ml). The product was dried at room temperature under vacuum to a constant weight. Yield: 18.61 g. Loss on drying (140° C.): 12.8%. Water content (Karl Fischer): 5.29%.

Example 7

The solution of 2,4-bis(4-methyl-1-piperazinyl)-3-propylidene-3H-[1,5]benzodiazepine (3 .805 g, 10 mmol) (prepared according to WO 2004/065390), pyridinium p-toluenesulfonate (5.026 g, 20 mmol) and sulfur (1.122 g, 35 mmol) in benzonitrile (100 ml) was stirred at 140° C. for 8.5 h, cooled to 90° C. and concentrated to an oily residue. The residue was diluted with isopropanol (50 ml) and dimethyl sulfoxide (5 ml). The precipitate was filtered off and washed with isopropanol (5 ml). Water (10 ml) and sodium hydroxide (1.00 g, 25 mmol) were added to the filtrate. The mixture was stirred at room temperature until the sodium hydroxide had dissolved. The turbid solution was left in a refrigerator over night resulting in a suspension. This was filtered off and washed with isopropanol (5 mL). The wet material was suspended in isopropanol (25 mL). and the suspension was heated to reflux. Then solids were hot filtered. Water (0.75 mL) was added to the filtrate to induce crystallization. The resulting suspension was cooled to 0° C., and upon completion of crystallisation, the product was filtered off and washed with isopropanol (1 mL). The product was then dried at room temperature under vacuum to a constant weight. Yield: 0.738 g.

Preparation of Olanzapine Methylene Chloride Hemisolvate

Example 8

Water-isopropanol mixed solvate of olanzapine (11 g) was suspended in methylene chloride (132 ml) and heated to obtain a clear solution. 66 ml of the solvent was distilled off. Another 16 ml of methylene chloride was added and distilled off. The mixture was hot filtered and concentrated under vacuum to a volume of 36 ml. During vacuum destination the solution was cooled and the product precipitated. The product was filtered off and dried under vacuum at room temperature to a constant weight. Yield: 8.47 g. Loss on drying (140° C.): 12.7%. Water,content (Karl Fischer): 0.40%.

Example 9

Olanzapine water-isopropanol mixed solvate (30 g) was suspended in methylene chloride (330 ml) and heated to 35° C. to obtain a clear solution. Drierite ($CaSO_4$ anhydrous, 45 g) was added and it was stirred for one hour. The suspension was hot filtered and concentrated under vacuum to a volume of 100 ml. During vacuum destillation the solution was cooled and the product precipitated. The product was filtered off and dried under vacuum at room temperature to a constant weight. Yield: 21.31 g. Loss on drying (140° C.): 11.3%. Water content (Karl Fischer): 0.51%.

Example 10

Olanzapine water-isopropanol mixed solvate (25 g) was suspended in methylene chloride (300 ml) and heated to obtain a clear solution. The mixture was concentrated at 25 to 30° C. under weak vacuum to 130 ml. The mixture was hot filtered and cooled to −20° C. The obtained suspension was filtered and the wet cake was dried under vacuum at room temperature to a constant weight. Yield: 17.7 g. Loss on drying (140° C.): 12.8%. Water content (Karl Fischer): 1.16%.

Example 11

Olanzapine water-isopropanol mixed solvate (30 g) was suspended in methylene chloride (360 ml) and the suspension was heated to obtain a clear solution. The solution was concentrated at 25 to 30° C. under weak vacuum to 180 ml. The mixture was hot filtered into a reactor made from perfluorated polymer and evaporated to dryness at room temperature under vacuum. The residue was dried under vacuum at room temperature to a constant weight. Yield: 27.5 g. Loss on drying (140° C.): 12.6%. Water content (Karl Fischer): 0.41%.

Example 12

Olanzapine water-isopropanol mixed solvate (50 g) was suspended in methylene chloride (600 ml) and the suspension was heated to obtain a clear solution. The solution was concentrated at 25 to 30° C. under a weak vacuum to 220 ml. The solution was then hot filtered and seeded with olanzapine form I. The suspension was cooled to −15° C. and solids were filtered off. The obtained wet cake was dried under vacuum at room temperature to a constant weight. Yield: 36.15 g. Loss on drying (140° C.): 12.7%. Water content (Karl Fischer): 0.57%.

Preparation of Olanzapine of Form I

In the following examples 13 to 17 olanzapine methylene chloride hemisolvate was used which. has been prepared according to any one of examples 8 to 12 which employ use of the water-isopropanol mixed solvate of olanzapine according to the invention.

In example 18 olanzapine water-isopropanol mixed solvate was used.

Example 13

Olanzapine methylene chloride hemisolvate (10 g) was suspended in isopropanol (20 ml). The suspension was stirred at room temperature for one hour. The product was filtered off and dried under vacuum at room temperature to a constant weight, and then at 50° C. to a constant weight. Yield: 7.8 g.

Example 14

Olanzapine methylene chloride hemisolvate (10 g) was suspended in isopropanol (150 ml, presaturated with olanzapine). The suspension was stirred at room temperature for one hour. The product was filtered off and dried under vacuum at room temperature to a constant weight, and then at 50° C. to a constant weight. Yield: 14.3 g.

Example 15

Olanzapine methylene chloride hemisolvate (6.00 g) was homogenized with olanzapine form I (0.30 g). The mixture was suspended in isopropanol (150 ml) and stirred at room temperature for 40 min. The suspension was filtered and the filter cake dried under vacuum at room temperature to a constant weight, and then at 50° C. to a constant weight. Yield: 4.63 g.

Example 16

Seeds of olanzapine form I were suspended in isopropanol (30 ml) and olanzapine methylene chloride hemisolvate (15 g) as well as isopropanol (7.5 ml) were added. The obtained suspension was stirred at room temperature for 30 min. The mixture was filtered and the separated solid was dried under vacuum at room temperature until a constant weight was achieved and then at 50° C. to a constant weight. The yield was 11.6 g.

Example 17

Olanzapine methylene chloride hemisolvate (20 g) was dried under vacuum at 50° C. for 12 hours.

10 g of the dried material were suspended in isopropanol (25 ml) and the mixture was stirred at room temperature for 20 min. The mixture was filtered and the separated solid was dried under vacuum at room temperature until a constant weight was achieved and then at 50° C. to a constant weight. The yield was 9 g.

Example 18

A mixture of olanzapine water-isopropanol mixed solvate (5 g) and olanzapine of form I (0.25 g) was grinded in a mortar. 5.071 g of the obtained material were dried in a vacuum drier at 50° C. for 16 h to yield 4.430 g of dried material. 3.5 g of the dried material were suspended in 8.8 ml of isopropanol, and the suspension was stirred at rcom temperature for 15 min. The obtained mixture was filtered and the separated solid was dried under vacuum until constant weight was achieved and then at 50° C. to constant weight.

The invention claimed is:

1. Isopropanol/water mixed solvate of olanzapine which contains 2 molecules of water and 1 molecule of isopropanol per 2 molecules of olanzapine.

2. The isopropanol/water mixed solvate of olanzapine of claim 1 characterized by the x-ray structure shown in FIG. 1.

3. The isopropanol/water mixed solvate of olanzapine of claim 1 characterized by a NMR spectrum in CDC1$_3$ showing peaks at approximately 1.20 ppm, 2.20-2. 40 ppm and 4.03 ppm.

4. The isopropanol/water mixed-solvate of olanzapine of claim 1 characterized by the NMR spectrum shown in FIG. 2.

5. A process for the preparation of the isopropanol/water mixed solvate of olanzapine according to claim 1, which comprises crystallizing it from a solvent mixture comprising isopropanol and water in a ratio of at least 9 to 1 parts by volume.

6. The process according to claim 5, wherein the solvent mixture comprises isopropanol and water in a ratio of at least 20 to 1 parts by volume.

7. The process according to claim 5, wherein the solvent mixture comprises isopropanol and water in a ratio of at least 35 to 1 parts by volume.

8. Process according to claim 5, wherein the crystallization is effected by adding the water to a solution comprising olanzapine and the isopropanol.

9. The process for the preparation of form I olanzapine, comprising dissolving the isopropanol/water mixed solvate according to claim 1 in an organic solvent to form a solution, and crystallizing or precipitating form I olanzapine or its precursor.

10. The process according to claim 9, wherein (a) the isopropanol/water mixed solvate is converted to a methylene chloride solvate of olanzapine, and (b) the methylene chloride solvate is converted to form I olanzapine.

11. The process according to claim 10, wherein in step (a) a solution of the isopropanol/water mixed solvate in methylene chloride is prepared, the solvent is partly evaporated and the remaining solution is cooled.

12. The process according to claim 10, wherein in step (a) a solution of the isopropanollwater mixed solvate in methylene chloride is prepared, a drying agent is added to the solution, the drying agent is removed from the mixture and the methylene chloride solvate of olanzapine is recovered.

13. The process according to claim 12, wherein anhydrous CaSO$_4$ is used as the drying agent.

14. The process according to claim 10, wherein the methylene chloride solvate is methylene chloride hemisolvate of olanzapine.

15. The process according to claim 10, wherein in step (b) the methylene chloride solvate is suspended in isopropanol.

16. The process according to claim 15, wherein the ratio between methylene chloride solvate (kg) and isopropanol (l) is 1:5 to 1:2.

17. The process according to claim 14, wherein in step (b) methylene chloride hemisolvate is dried under vacuum at a temperature of 30 to 55 C for 6 to 36 hours, the dried hemisolvate is suspended in isopropanol, the suspension is stirred at a temperature of 15 to 35 C for 15 to 60 min, and the form I olanzapine is separated.

18. The process according to claim 9, wherein the solid isopropanollwater mixed solvate of olanzapine is mixed with solid olanzapine of form I and the particle size of the mixture is reduced.

19. The process according to claim 18, wherein the mixture comprises up to 10% by weight of form I olanzapine.

20. The process according to claim 18, wherein the mixture of reduced particle size is dried in a vacuum drier at temperatures ranging from room temperature to 80 C.

21. The process according to claim 20, wherein the dried material is suspended in isopropanol, the solid is separated by filtration and dried.

22. The process according to claim 21, wherein the dried material is suspended in isopropanol in a weight (kg) to volume (l) ratio of 1:5 to 1:2, in particular 1:3 to 1:2.

23. The process for the preparation of an anhydrous form of olanzapine, comprising dissolving isopropanol/water mixed solvate of olanzapine according to claim 1 and precipitating the anhydrous form of olanzapine.

24. A process for preparing form I olanzapine, wherein at least one of (a) a precursor for olanzapine form 1 and (b) olanzapine form I is crystallized or precipitated from a liquid medium which medium is present in a container wherein the surfaces of the container contacting the medium are comprising at least one polymer.

25. The process according to claim 24, wherein a precursor for olanzapine form 1 is crystallized or precipitated.

26. The process according to claim 25, wherein the precursor is methylene chloride hemisolvate of olanzapine.

27. The process according to claim 24, wherein the precursor or the olanzapine form T has been prepared using the isopropanollwater mixed solvate of olanzapine which contains 2 molecules of water and 1 molecule-of isopropanol per 2 molecules of olanzapine.

28. Process according to claim 24, wherein the surfaces of the container contacting the medium are consisting of at least one polymer.

29. The process according to claim 24, wherein the polymer contains fluorine.

30. The process according to claim 24, wherein the polymer is selected from polytetrafluoroethylene, fluorinated ethylene propylene copolymer, perfluor alkoxy polymer, or ethylene tetrafluoroethylene copolymer.

* * * * *